United States Patent [19]

Thompson

[11] 4,112,353
[45] Sep. 5, 1978

[54] METHOD FOR TESTING DIELECTRIC ADEQUACY AND FOR INDICATING PHYSICAL DEFECTS IN A NONCONDUCTING MATERIAL BY DEPOSITING TRACES OF CARBON ON THE MATERIAL

[75] Inventor: Robert W. Thompson, Pearland, Tex.

[73] Assignee: Westinghouse Electric Corp., Pittsburgh, Pa.

[21] Appl. No.: 725,314

[22] Filed: Sep. 21, 1976

Related U.S. Application Data

[62] Division of Ser. No. 603,074, Aug. 8, 1975, Pat. No. 4,010,416.

[51] Int. Cl.$^2$ ............................................. G01R 31/12
[52] U.S. Cl. .................................................... 324/54
[58] Field of Search ........................................... 324/54

[56] References Cited

U.S. PATENT DOCUMENTS

| | | | |
|---|---|---|---|
| 1,427,817 | 9/1922 | Hutchinson | 324/54 X |
| 2,501,676 | 3/1950 | Ives | 324/54 |
| 3,069,620 | 12/1962 | Servos | 324/54 |
| 3,417,327 | 12/1968 | Breidenbach | 324/54 |
| 3,555,414 | 1/1971 | Deichelmann | 324/54 |
| 3,719,884 | 3/1973 | Laroche | 324/54 |
| 3,735,251 | 5/1973 | Britton | 324/54 |
| 3,943,438 | 3/1976 | Barber et al. | 324/54 |
| 3,965,415 | 6/1976 | Ehret | 324/54 |

OTHER PUBLICATIONS

Macentyre, A. D. *Glove Tester and Drier that Save Time,* Electrical World, vol. 89, No. 11, Mar. 12, 1927, p. 561.

*Primary Examiner*—Gerard R. Strecker
*Attorney, Agent, or Firm*—F. J. Baehr, Jr.

[57] ABSTRACT

An elastomer impregnated with carbon is utilized in conjunction with a conductor to test the dielectric adequacy of a nonconductor and to indicate physical defects, such as cracks, pinholes or a thickness below a predetermined minimum, by depositing traces of carbon on the nonconductor in the area of the defect or the area where the thickness is below the predetermined minimum.

2 Claims, 10 Drawing Figures

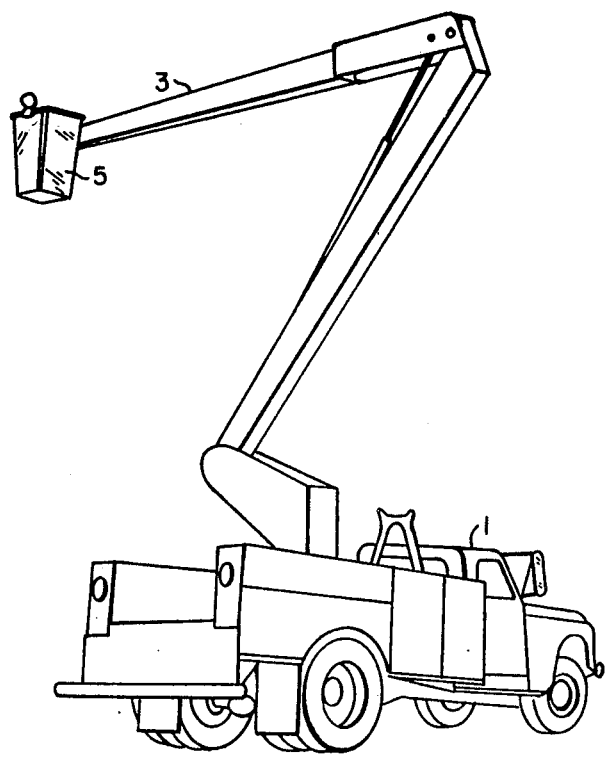
FIG.1
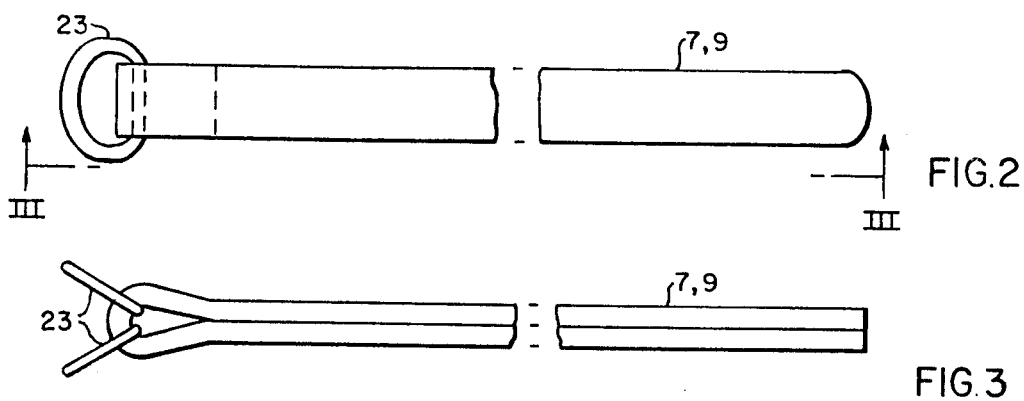
FIG.2
FIG.3

METHOD FOR TESTING DIELECTRIC ADEQUACY AND FOR INDICATING PHYSICAL DEFECTS IN A NONCONDUCTING MATERIAL BY DEPOSITING TRACES OF CARBON ON THE MATERIAL

This is a division, of application Ser. No. 603,074 filed Aug. 8, 1975, now U.S. Pat. No. 4,010,416.

BACKGROUND OF THE INVENTION

This invention relates to a method and apparatus for testing nonconductive materials and particularly to testing fiber reinforced resin materials for physical and electrical soundness.

Trucks carrying an articulated aerial device or a boom for lifting a man-carrying bucket or basket are often positioned in the proximity of high-voltage power lines and are intended to insulate men located in the baskets from ground or from other nearby high-voltage lines should the boom or basket inadvertently touch some high-voltage line or a ground wire.

To insure the dielectric adequacy of the basket and boom, it is desirable to check the conductivity of the basket and boom; however, electrical shock is not the only danger to which men working in baskets are subjected. There can be latent structural defects in the boom or basket, which will cause it to fail and it is known that sunlight has a deleterious effect on plastic resins, which will cause a gradual degradation of the physical properties or strength of the material. Thus, apparatus and methods for testing the dielectric adequacy, as well as structural soundness of such booms and baskets are a necessity to insure the safety of those who utilize this equipment to maintain the power lines.

SUMMARY OF THE INVENTION

In general, the method and apparatus utilized to test a nonconductor for dielectric adequacy and for physical defects when made in accordance with this invention, comprises utilizing an elastomer impregnated or filled with particulate conducting material as a first conductor in conjunction with a second conductor, the conductors being such that they are in intimate contact with the material to be tested and imposing a DC voltage across the conductors and increasing the voltage at a linear rate to a predetermined value, indicating the voltage as it is increased and indicating the current as the voltage increases. This invention also incorporates responding to a nonlinear increase in the rate of increase of current relative to a linear increase in voltage to decrease the rate at which the voltage is increased and continuing to increase the voltage at a much slower rate until there is a visible mark on the nonconductor outlining a defect or a smudge appears indicating a thickness below a minimum predetermined thickness.

BRIEF DESCRIPTION OF THE DRAWINGS

The objects and advantages of this invention will become more apparent from reading the following detailed description in connection with the accompanying drawings, in which corresponding reference characters indicate corresponding portions throughout the drawings and in which:

FIG. 1 is an elevational view of a boom and basket mounted on a truck indicating typical equipment that may be tested utilizing the apparatus and method described in this invention;

FIG. 2 is a plan view of a belt utilized as an electrode in this invention;

FIG. 3 is a sectional view taken on line III—III of FIG. 2;

DESCRIPTION OF THE PREFERRED EMBODIMENTS

Figure 4:
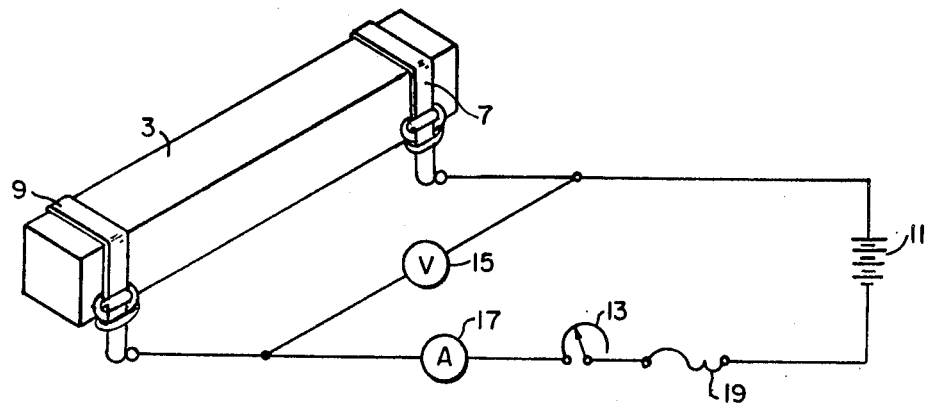
FIG. 4 is a schematic drawing of apparatus made in accordance with this invention for testing a portion of a boom.
Figure 5:
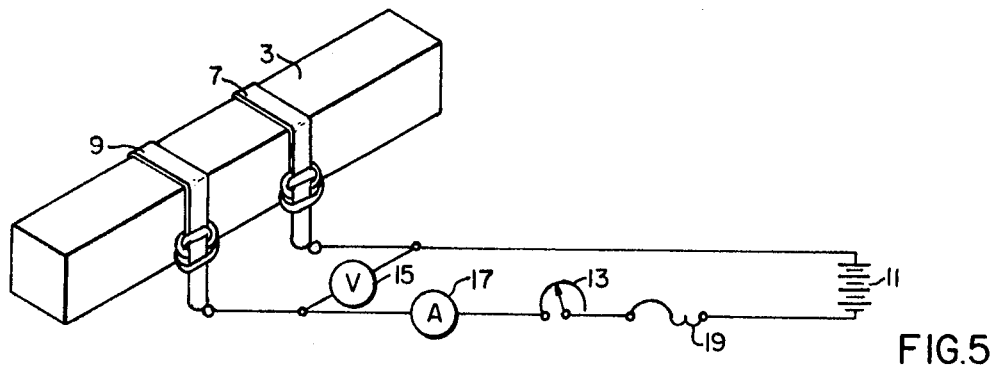
FIG. 5 is a schematic drawing of apparatus made in accordance with this invention for testing a portion of a boom for physical defects.

Referring now to the drawings, and in particular to FIG. 1, there is shown a truck 1 having a boom or articulated aerial device 3 to which a bucket, basket, vessel or cockpit 5, which is suitable for transporting a man, is pivotally attached. Such devices are commonly utilized by utility companies to raise workmen to elevated positions to work on poles, light standards, transformers, electrical lines and/or other elevated devices. While this invention is particularly applicable to testing such devices for dielectric adequacy and for physical defects, it is not limited thereto, but may be utilized to test any generally nonconductive material, one particular type of material being a fibrous reinforced material commonly referred to as fiberglass. However, the invention is not limited to testing this particular material but may be utilized on any nonconducting material.

As shown in FIGS. 4 through 10, the testing apparatus comprises a first conductor or electrode 7, 7a or 7b and a second conductor or electrode, 9, 9a, 9b or 9c. As shown in these schematic drawings, the testing apparatus also comprises a DC source capable of producing a variable DC voltage, which generally varies between 0 and 100,000 volts or higher and is indicated schematically by the battery symbol 11 and a variable resistor 13, a DC voltage meter 15 or other means for indicating the voltage produced by the power source, and a DC amp meter 17 capable of indicating current in micro- and/or milliampere ranges. Some type of protective device, such as a circuit breaker, indicated at 19 is also incorporated in the power supply and limits the flow of current in the test circuit. The electrodes 7 and 9, as shown in FIGS. 2 and 3, are formed from belts or strips of elastomer material filled with a particulate conducting material, such as carbon. The strips preferably have rounded ends 21 and are folded in half. A pair of D-shaped buckles 23 are disposed adjacent the fold and the overlapping portions of the strips are bonded together by an adhesive or other means to form an elastomer belt, which may be pulled tight and buckled in place. The electrodes 7a and 9a are ionic solutions capable of conducting an electrical current and may comprise a plate 24 to provide a large contact surface within the ionic fluid. The electrodes or conductors 7b and 9b are pads which generally conform to the shape of the nonconductor. They may be elastomer pads filled with particulate conducting material; or they may be felt pads, cloth or paper pads, saturated with an ionic solution.

Figure 7:
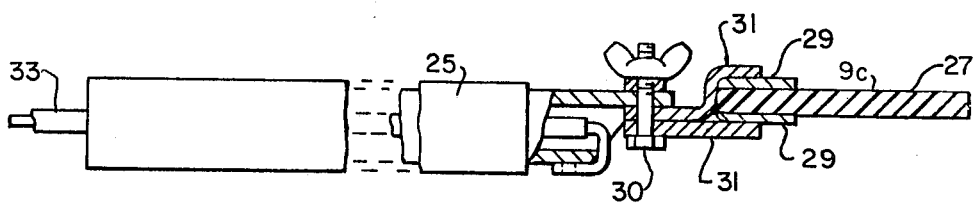
FIG. 7 is a partial sectional view taken on line VII—VII of FIG. 6.
Figure 6:
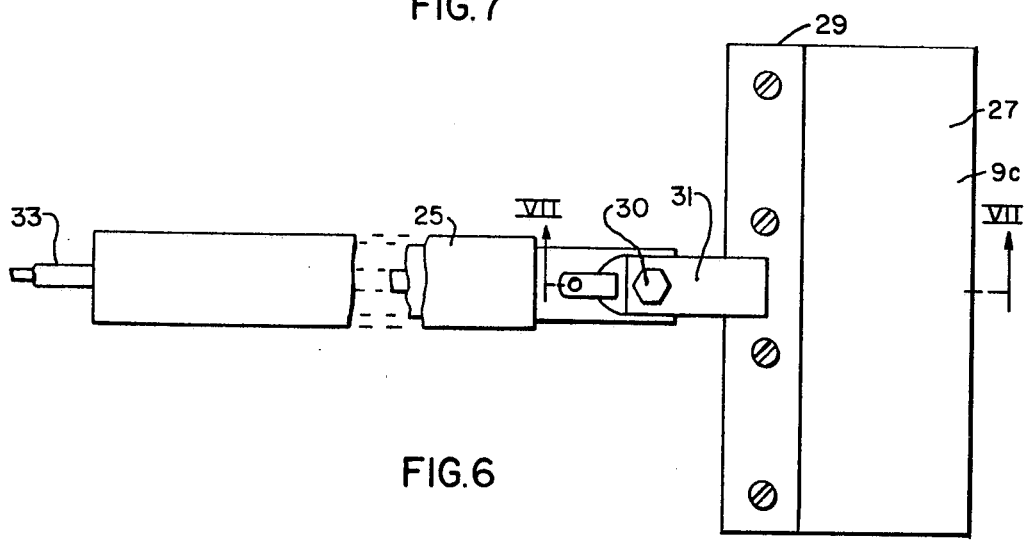
FIG. 6 is a plan view of a conductive wand utilized in this invention.

The electrode 9c, as shown in FIGS. 6 and 7, comprises an elastomer strip impregnated or filled with particulate conducting material, such as carbon, fastened to a nonconducting handle 25 in such a way as to form a wiper blade 27. The wiper blade 27 is generally a rectangular shaped slab of elastomer material impregnated with carbon clamped by a pair of flat bars 29 which are disposed along one longitudinal margin of the wiper blade 27. A machine screw 30 or other clamping device cooperates with a pair of clamping bars 31 to connect the flat bars 29 to the handle 25, providing a hand-held wiper or wand 27, which may be wiped across the object to be tested. An insulated wire 33 passes through the handle and is electrically connected to the wiper blade 27 through the clamping means 31 and flat bars 29.

Figure 8:
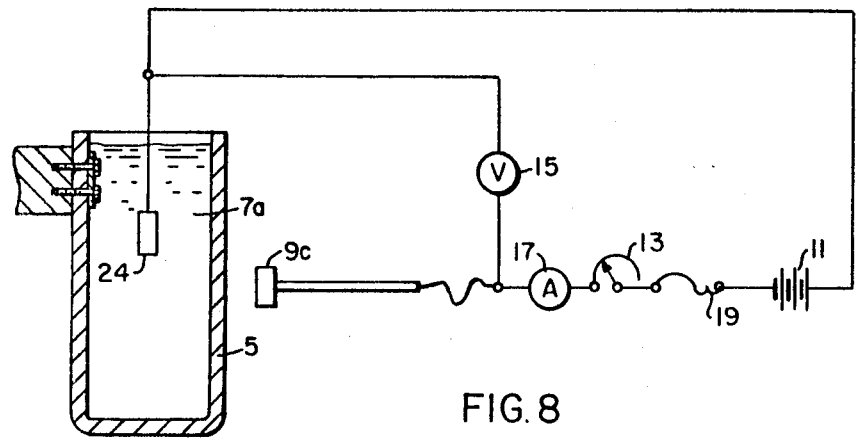
FIG. 8 is a schematic drawing of apparatus made in accordance with this invention for testing the dielectric adequacy and the physical soundness of a basket.
Figure 9:
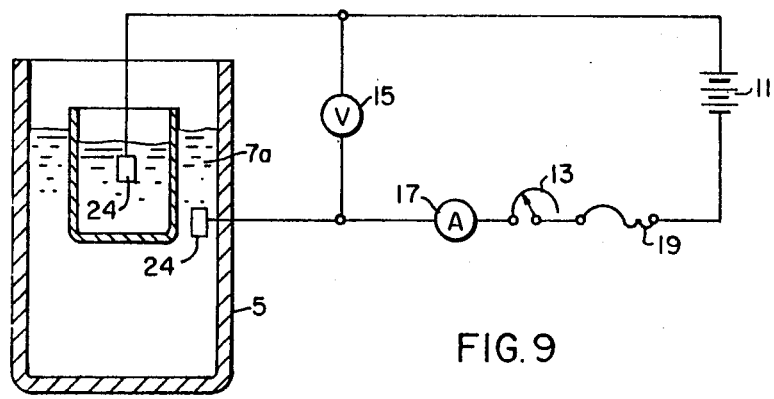
FIG. 9 is a schematic drawing of apparatus made in accordance with this invention for testing a nonconductor for dielectric adequacy and for physical defects.
Figure 10:
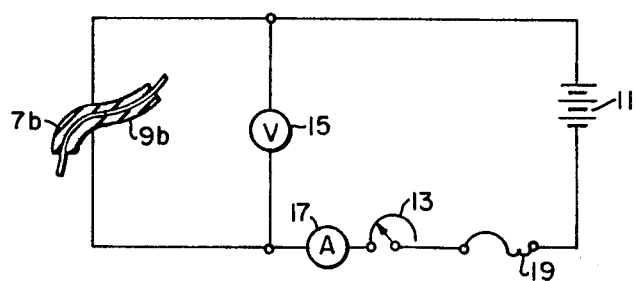
FIG. 10 is a schematic drawing of apparatus made in accordance with this invention and utilized to test a nonconductor for dielectric adequacy and for physical defects.

A method for utilizing the apparatus hereinbefore described to test a nonconducting material for dielectric adequacy and for physical defects, such as pinholes, cracks and inclusion of conductive material, generally comprises the following steps:

placing the first conductor 7, 7a, or 7b adjacent the nonconductor;

placing the second conductor 9, 9a, 9b or 9c adjacent the nonconductor in a spaced relationship with the first conductor, depending on the shape of the nonconductor different types of conductors would be utilized. For beams or rectangular, triangular, round or other regular cross-section, the elastomer belts 7 and 9, as shown in FIGS. 2 and 3, are preferred. Whereas to check baskets, boats or other vehicles, the conductors may comprise an ionic solution, such as indicated in FIGS. 8 and 9 or a felt cloth or paper pad which conforms to the irregular shape and is saturated with an ionic solution, as indicated in FIG. 10, may also be utilized. The wipers 27, as shown in FIGS. 6 and 7, could be utilized with any of the above and the wiper could be shaped for a particular purpose.

The steps further comprise connecting individually leads or lines from a variable DC voltage power source capable of producing from 0 to 100,000 volts or higher to each conductor, one of the leads also being grounded;

generally increasing the DC voltage between the conductor to approximately 100,000 volts or some predetermined value, depending on the nonconductor and the relative location of the conductors, linearly or at a predetermined generally constant rate, for example, increasing from 0 to 100,000 volts in thirty seconds;

indicating the DC voltage between the conductors as the voltage is increased utilizing the voltage meter 15;

indicating the current flowing between the conductors by utilizing the amp meter 17;

holding the voltage at the predetermined level for a specific period of time, for example, three minutes to indicate the dielectric adequacy of the nonconductor;

responding to a nonlinear increase in current relative to a linear increase in voltage to decrease the rate at which the voltage is increased, whereby the voltage is increased at a much slower rate until there is a visible mark on the nonconductor which generally outlines the defect, the mark being made by the filler material.

This invention also includes a method for testing the nonconductive portion of an articulating arm or boom of an aerial lift truck and comprises the steps of:

placing a first conducting belt 7 around the boom adjacent one end thereof;

pulling the belt tight so that it is in intimate contact with the boom;

buckling the belt so that it doesn't slip and loosen;

placing a second conducting belt 9 around the boom adjacent the other end thereof;

pulling the belt 9a tight so that it is in intimate contact with the boom;

buckling the belt so that it does not loosen and slip;

connecting individual leads from a variable DC voltage supply capable of supplying 0 to 100,000 volts DC or more to the belts 7 and 9;

grounding the truck, one belt and one of the leads from the DC supply;

increasing the voltage between the belts at a generally linear rate until it reaches some predetermined voltage, for example, from 0 to 100,000 volts in thirty seconds;

leaving the voltage at the predetermined level for a predetermined time interval, approximately three minutes;

reducing the voltage to 0 and grounding the belts;

then moving one of the belts so that it is generally parallel to the other belt and a short distance therefrom, approximately eighteen inches;

connecting the leads from the DC power supply to the belts;

increasing the DC voltage between the belts to a predetermined value at a generally linear rate;

indicating the voltage as it is being increased;

indicating the current as the voltage is being increased;

responding to a nonlinear increase in the rate at which the current increases relative to a linear increase in voltage to decrease the rate at which the voltage is increased;

continuing to increase the DC voltage at a reduced rate until a mark appears on the nonconductive boom, the mark indicating the outline and location of a physical defect;

successively reducing the voltage across the belts to 0;

grounding the belts and moving at least one belt at a time so as to check each incremental portion of the boom by increasing the voltage at a linear rate to a predetermined voltage and responding to a nonlinear increase in current flowing between the electrodes or belts to reduce the rate at which the voltage is increased and increasing the voltage at the much lower rate until a mark appears on the boom, indicating the outline and location of a defect within that portion of the boom.

This invention also incorporates a method for testing a container for dielectric adequacy and for physical defects and comprises the steps of:

placing an ionic solution in the container so that it fills at least a portion thereof;

placing a first electrode in the solution;

connecting a supply of DC voltage to the first and to a second electrode, the second electrode also being connected to ground and having a wiper blade formed from an elastomer filled with a conductive particulate conductor material;

imposing a predetermined DC voltage across the electrodes;

passing the wiper portion of the second electrode over the outer side of that portion of the container containing the ionic solution;

whereby the particulate material in the wiper electrode will leave marks outlining physical defects and smudges in the area where the thickness is below a predetermined value;

raising the container and passing the wiper portion of the second electrode over the lower portion thereof;

supporting the lower portion of the container so that it may be filled with ionic solution and passing the wiper portion of the second electrode over the outer portion of that portion of the container containing the ionic fluid, whereby the particulate material from the wiper blade will deposit on the surface of the container and outline of the physical defects and make smudges where the thickness thereof is below a predetermined value.

The method described above for testing a container is intended to include any container, a basket for an aerial lift truck, boat hull, an amusement vehicle or cockpit, or any other container or shape which will hold a liquid and is made from a nonconductive material where it is desirable to test for either dielectric adequacy and/or for physical defects or for minimum thickness.

This invention also includes a method for testing a plastic or resinous material for deterioration due to exposure to sunlight and other atmospheric conditions, including the steps of:

placing a first conductor which generally conforms to the area to be tested on one side of this area. The first conductor may be an ionic solution as shown in FIG. 8, or as shown in FIG. 10 it may be an elastomer filled with a particulate conductor, such as carbon, or the first conductor may be an absorbent pad, such as felt, cloth or paper, saturated with the ionic solution so long as it generally conforms to the shape of the area to be tested;

connecting the first conductor and a conductor having a wiper blade to a DC power source;

imposing a predetermined DC voltage across the first conductor and the wiper blade;

passing the wiper blade over the area to be tested, whereby marks will appear outlining physical defects and smudges will appear in areas where the thickness is below a minimum value;

if no physical defects appear, then reducing the voltage to 0 and grounding the wiper and the first conductor;

placing another or third conductor, which generally conforms to the area to be tested, on the side opposite the one side having the first conductor, the third conductor may be an ionic solution as shown in FIG. 9, or as shown in FIG. 10 an elastomer filled with a conductor or an absorbent pad saturated with an ionic solution;

applying a predetermined DC voltage across the conductors and recording the current flowing therebetween;

utilizing the plastic or resinous material whereby it is exposed to sunlight or other atmospheric conditions, then after a certain time interval, which may be as long as a year or more, retesting the plastic or resinous material by placing the first conductor, which generally conforms to the area to be tested on one side of the area;

connecting the first conductor and a conductor having a wiper blade to a DC power source;

imposing a predetermined DC voltage across the first conductor and the wiper blade;

passing the wiper blade over the area to be tested, whereby marks will appear outlining physical defects;

if no physical defects are present, placing a third conductor which generally conforms to the area to be tested on the side opposite the one side having the first conductor;

applying a predetermined DC voltage across the conductors;

recording the current flowing therebetween;

comparing this latest reading with the previous reading, the amount of current flowing between the conductors being an indication of the deterioration of the dielectric properties of the plastic or resinous material due to exposure to sunlight and other atmospheric conditions which is also an indication of the deterioration of the physical properties, such as strength and ductility of the plastic or resinous material so that when the current flowing between the electrodes reaches some predetermined level, the physical properties of the material have reached a level that the material is no longer safe for use or continued exposure to sunlight and other atmospheric conditions, will soon render it unsafe for use.

The method and apparatus hereinbefore described advantageously tests nonconductive material for dielectric adequacy, physical defects, such as cracks, pinholes, inclusion of conductive material, and a thickness below a minimum amount, and these methods and apparatus can also be utilized to indicate the degradation of the physical properties such as the strength and ductility of the material due to its exposure to sunlight and other atmospheric conditions by making comparisons of the changes in the dielectric characteristics of the material due to this exposure. The nondestructive tests hereinbefore described assure the physical and dielectric adequacy of resinous and plastic materials utilized to carry men for work or pleasure.

What is claimed is:

1. A method for testing a personnel container for physical defects and dielectric adequacy, comprising the steps of:

placing an ionic solution in the container;

placing a first electrode in said solution;

passing a second electrode having a wiper blade formed from an elastomer filled with conductive particulate material over the outer portion of said container which is filled with said ionic solution;

imposing a predetermined DC voltage across said electrodes, and determining the location of a mark of smudge on said container, said particulate material in the elastomer leaving a mark outlining a defect or a smudge if the thickness is below some minimum value.

2. The method as set forth in claim 1, and further comprising the step of raising the container and passing the second electrode over the bottom of the container, whereby physical defects are made obvious by the deposition of particulate material on the surface of the nonconductive material.

* * * * *